(12) United States Patent  
Linares

(10) Patent No.: US 8,828,088 B2  
(45) Date of Patent: Sep. 9, 2014

(54) JOINT ASSEMBLY INCORPORATING UNDERCUT SURFACE DESIGN TO ENTRAP ACCUMULATING WEAR DEBRIS FROM PLASTIC JOINT ASSEMBLY

(75) Inventor: Miguel A. Linares, Bloomfield Hills, MI (US)

(73) Assignee: Linares Medical Devices, LLC, Auburn Hills, MI (US)

( * ) Notice: Subject to any disclaimer, the term of this patent is extended or adjusted under 35 U.S.C. 154(b) by 518 days.

(21) Appl. No.: 12/776,903

(22) Filed: May 10, 2010

(65) Prior Publication Data

US 2010/0222892 A1 Sep. 2, 2010

Related U.S. Application Data

(63) Continuation-in-part of application No. 12/266,695, filed on Nov. 7, 2008.

(60) Provisional application No. 60/986,486, filed on Nov. 8, 2007, provisional application No. 61/183,736, filed on Jun. 3, 2009.

(51) Int. Cl.
*A61F 2/30* (2006.01)
*A61F 2/38* (2006.01)
*A61F 2/08* (2006.01)
*A61F 2/32* (2006.01)

(52) U.S. Cl.
CPC ... *A61F 2/30771* (2013.01); *A61F 2002/30823* (2013.01); *A61F 2/30965* (2013.01); *A61F 2002/30971* (2013.01); *A61F 2002/30937* (2013.01); *A61F 2/38* (2013.01); *A61F 2/08* (2013.01); *A61F 2002/30807* (2013.01); *A61F 2/3804* (2013.01); *A61F 2002/30934* (2013.01); *A61F 2002/30673* (2013.01); *A61F 2/32* (2013.01); *A61F 2002/30682* (2013.01); *A61F 2002/30827* (2013.01)
USPC ............. 623/22.15; 623/18.11; 623/20.22; 623/21.13; 623/21.16; 623/16.11

(58) Field of Classification Search
CPC ....................... A61F 2002/30026; A61F 2/30
USPC .......... 623/23.39, 14.12, 22.17, 22.21, 22.33, 623/23.5, 16.11, 18.11, 20.13, 20.15, 20.16, 623/20.18, 20.21, 20.22, 22.11, 23.4, 23.42, 623/23.46
See application file for complete search history.

(56) References Cited

U.S. PATENT DOCUMENTS

| | | |
|---|---|---|
| 2,667,644 A | 2/1954 | Johnson |
| 3,651,521 A | 3/1972 | Devas |
| 3,798,679 A | 3/1974 | Ewald |
| 3,875,594 A | 4/1975 | Swanson |

(Continued)

FOREIGN PATENT DOCUMENTS

JP 07116184 A 5/1995

*Primary Examiner* — Thomas J Sweet
*Assistant Examiner* — Seema Mathew
(74) *Attorney, Agent, or Firm* — Gifford, Krass, Sprinkle, Anderson & Citkowski, P.C.; Douglas J. McEvoy

(57) ABSTRACT

A layer applied to a joint defined surface including a general mat shape body exhibiting a plurality of recesses, such that abrading contact with an opposing joint surface creates debris which are entrapped within the recesses during a normal range of motion. The body can further exhibit a first harder plastic substratum and a second softer plastic surface. The recesses further incorporate undercut defined patterns selected from any of circular, linear and arcuate designs.

5 Claims, 3 Drawing Sheets

(56) References Cited

U.S. PATENT DOCUMENTS

| | | |
|---|---|---|
| 3,964,106 A | 6/1976 | Hutter, Jr. et al. |
| 4,215,439 A | 8/1980 | Gold et al. |
| 4,231,122 A | 11/1980 | Koeneman |
| 4,367,562 A | 1/1983 | Gauthier et al. |
| 4,538,305 A | 9/1985 | Engelbrecht et al. |
| 4,714,477 A | 12/1987 | Fichera et al. |
| 4,865,603 A * | 9/1989 | Noiles ......................... 623/23.5 |
| 4,964,868 A | 10/1990 | Bloebaum |
| 4,990,161 A | 2/1991 | Kampner |
| 5,007,934 A | 4/1991 | Stone |
| 5,021,061 A | 6/1991 | Wevers et al. |
| 5,092,898 A | 3/1992 | Bekki et al. |
| 5,171,325 A | 12/1992 | Aulie |
| 5,197,987 A | 3/1993 | Koch et al. |
| 5,389,107 A | 2/1995 | Nassar et al. |
| 5,462,362 A | 10/1995 | Yuhta et al. |
| 5,509,934 A | 4/1996 | Cohen |
| 5,549,701 A * | 8/1996 | Mikhail ..................... 623/22.21 |
| 5,553,476 A | 9/1996 | Oehy et al. |
| 5,571,193 A | 11/1996 | Kampner |
| 5,593,445 A | 1/1997 | Waits |
| 5,645,601 A | 7/1997 | Pope et al. |
| 5,662,158 A | 9/1997 | Caldarise |
| 5,676,702 A | 10/1997 | Ratron et al. |
| 5,728,175 A | 3/1998 | Rincoe |
| 5,800,566 A | 9/1998 | Gramnas et al. |
| 5,879,406 A | 3/1999 | Lilley |
| 5,916,269 A | 6/1999 | Serbousek et al. |
| 5,921,358 A | 7/1999 | Gramnas et al. |
| 6,005,103 A * | 12/1999 | Domagala et al. ............... 544/60 |
| 6,045,581 A | 4/2000 | Burkinshaw |
| 6,165,223 A | 12/2000 | Metzger et al. |
| 6,398,815 B1 | 6/2002 | Pope et al. |
| 6,627,141 B2 | 9/2003 | McNulty et al. |
| 6,660,040 B2 | 12/2003 | Chan et al. |
| 6,692,679 B1 | 2/2004 | McNulty et al. |
| 6,723,102 B2 | 4/2004 | Johnson et al. |
| 6,800,298 B1 | 10/2004 | Burdick et al. |
| 6,800,670 B2 | 10/2004 | Shen et al. |
| 6,811,568 B2 | 11/2004 | Minamikawa |
| 6,818,172 B2 | 11/2004 | King et al. |
| 6,866,685 B2 | 3/2005 | Chan et al. |
| 6,962,607 B2 | 11/2005 | Gundlapalli et al. |
| 7,044,983 B1 | 5/2006 | Cheng et al. |
| 7,066,958 B2 | 6/2006 | Ferree |
| 7,087,091 B1 | 8/2006 | Chen et al. |
| 7,109,181 B2 | 9/2006 | Cowlen et al. |
| 7,148,209 B2 | 12/2006 | Hoemann et al. |
| 7,175,666 B2 | 2/2007 | Yao |
| 7,179,298 B2 | 2/2007 | Greenlee |
| 7,186,364 B2 | 3/2007 | King et al. |
| 7,331,995 B2 | 2/2008 | Eisermann et al. |
| 7,384,430 B2 | 6/2008 | Greer et al. |
| 7,578,851 B2 | 8/2009 | Dong et al. |
| 7,758,653 B2 * | 7/2010 | Steinberg ..................... 623/23.5 |
| 7,771,485 B2 | 8/2010 | Grundei |
| 7,780,738 B2 | 8/2010 | Khandkar et al. |
| 8,070,823 B2 * | 12/2011 | Kellar et al. ................. 623/23.4 |
| 2002/0183845 A1 * | 12/2002 | Mansmann ................. 623/13.11 |
| 2003/0065401 A1 | 4/2003 | Amrich et al. |
| 2003/0216669 A1 | 11/2003 | Lang et al. |
| 2004/0024460 A1 | 2/2004 | Ferree |
| 2004/0034433 A1 * | 2/2004 | Chan et al. ................. 623/23.39 |
| 2004/0068322 A1 | 4/2004 | Ferree |
| 2005/0055100 A1 | 3/2005 | Lewis et al. |
| 2005/0119758 A1 * | 6/2005 | Alexander et al. ........... 623/23.5 |
| 2005/0171604 A1 | 8/2005 | Michalow |
| 2005/0177248 A1 * | 8/2005 | Hall ....................... 623/23.56 |
| 2005/0192672 A1 | 9/2005 | Wyss et al. |
| 2005/0192674 A1 | 9/2005 | Ferree |
| 2005/0202371 A1 * | 9/2005 | McGuire .................... 433/201.1 |
| 2005/0287187 A1 | 12/2005 | Mansmann |
| 2007/0179613 A1 | 8/2007 | Heinz |
| 2007/0287027 A1 | 12/2007 | Justin et al. |
| 2008/0033567 A1 | 2/2008 | Stchur |
| 2008/0288081 A1 | 11/2008 | Scrafton et al. |
| 2009/0076605 A1 | 3/2009 | Linares |
| 2009/0125108 A1 | 5/2009 | Linares |

* cited by examiner

JOINT ASSEMBLY INCORPORATING UNDERCUT SURFACE DESIGN TO ENTRAP ACCUMULATING WEAR DEBRIS FROM PLASTIC JOINT ASSEMBLY

CROSS-REFERENCE TO RELATED APPLICATIONS

This Application is a Continuation-in-part of application Ser. No. 12/266,695 filed on Nov. 7, 2008, which application claims the benefit of U.S. Provisional Application 60/986,486 filed on Nov. 8, 2007. This Application also claims the benefit of U.S. Provisional Application 61/183,736 filed on Jun. 3, 2009.

FIELD OF THE INVENTION

The present invention discloses a supporting surface associated with either of male and/or female portions of an artificial joint and which includes a type of recess/undercut pattern incorporated into the wear surface for entrapping and removing worn away debris arising from abrading contact with an opposing plasticized joint defined surface.

BACKGROUND OF THE INVENTION

The prior art is documented with varying types of joint assemblies, include implants applied to the knee, elbow and hip. Artificial implants can further include any of durable titanium, other metal, or a polymeric material including a nylon or like wear resistant material which is established within a wear zone created between such as a male (ball) and female (receiver or pocket) forming in particular a hip or knee type joint.

Despite advances in artificial implant technology, it is still found that in situ aggregations of microscopic sized particles progressively worn away from the contact surfaces through normal joint motion can, over time impair or compromise the effectiveness of the joint. This further necessitates remedial surgery in order to suction (scope) the implant zone in an attempt to remove time elapsed aggregations of microscopic wear particles.

SUMMARY OF THE PRESENT INVENTION

The present invention discloses a modification to such artificial implant assemblies in the prevention of joint degradation resulting from accumulated wear particles (which is defined to include any of metal and/or polymeric particle sized shavings resulting from surface contact established between bone and/or bone to metal or plastic covered implant layers) and which discloses an outermost wear layer applied to a joint defined surface. The wear layer includes a generally mat shape body exhibiting a plurality of interiorly (undercut and otherwise configured) recesses.

In normal use, abrading contact with an opposing joint surface associated with the joint implant creates debris which, as opposed to contaminating the joint zone, instead are entrapped within the multitude of pockets established within the recesses during a normal range of motion. The body can further exhibit a first harder plastic substratum and a second softer plastic surface. The recesses further incorporate undercut defined patterns selected, without limitation, from any of circular, linear and arcuate designs and which are designed to optimize collection and retention of progressively abraded/ sheared wear particles in non-interfering fashion to the continued operation of the artificial implant/wear joint.

BRIEF DESCRIPTION OF THE DRAWINGS

Reference will now be made to the attached drawings, when read in combination with the following detailed description, wherein like reference numerals refer to like parts throughout the several views, and in which.

DETAILED DESCRIPTION OF THE PREFERRED EMBODIMENTS

The present invention discloses a series of uniquely configured debris removal surfaces incorporated into any type of artificially implanted or retrofit resurfaced joint (this further defined as an existing or organic joint which has been damaged but is end resurfaced, such as during an in situ operation) in the attempt to continue its wear life. A plasticized layer, such as constructed of an antimicrobial plastic but including any type of composite or other polymeric material, is applied upon opposing end faces established upon first and second joint defined bones and such that, in use, the layer coacts with an opposing end face of a further selected bone.

In particular the several embodiments of the present invention as described herein include mat structures exhibiting such as a generally plastic/polymer based material exhibiting a generally planar and flexible/deformable construction, and into which is entrained smaller volumes (such as according to a graded particulate) of a graphite/carbon and a ceramic/metallic impregnate material. Although not shown, it is envisioned that the construction of the flexible and joint defining end surface is such that it aggregates and evenly distributes across its surface area such as a natural lubricant fluid produced by the body. It is also envisioned that additional embodiments of the mat design can augment or (in certain instances) replace the natural fluid retention capabilities with a synthetic lubricant, and such as which can be introduced by external injection or internally provided secretion processes.

The plasticized layers as known may exhibit a polymeric based mat exhibiting a selected length, width and thickness for filling a three dimensional area associated with the joint location. It is further known that each of the plasticized mats may also include a first additive selected from at least one of a carbon and a graphite, and a second additive selected from at least one of a ceramic and a metal for providing the flexible and polymeric based mat with enhanced wear resistant properties. The opposing bone structure may also establish a joint selected from a group including at least one of upper/lower knee joint and an outer/inner ball and socket joint.

Although not shown additional structure such as ligaments, tendons and the like are understood to be incorporated into the joint assembly, and which include either or both of natural or synthetically implanted items. As is further known, contact between opposing bone surfaces within the artificial and/or retrofit joint invariably results over time in abrading wear-away of material from a selected plastic/mat layer. As previously described, the resulting build-up of wear debris invariably degrades joint performance over time absent provision of an effective mechanism in place for segregating/removing the built up debris from the wear surfaces of the joint.

Figure 1:
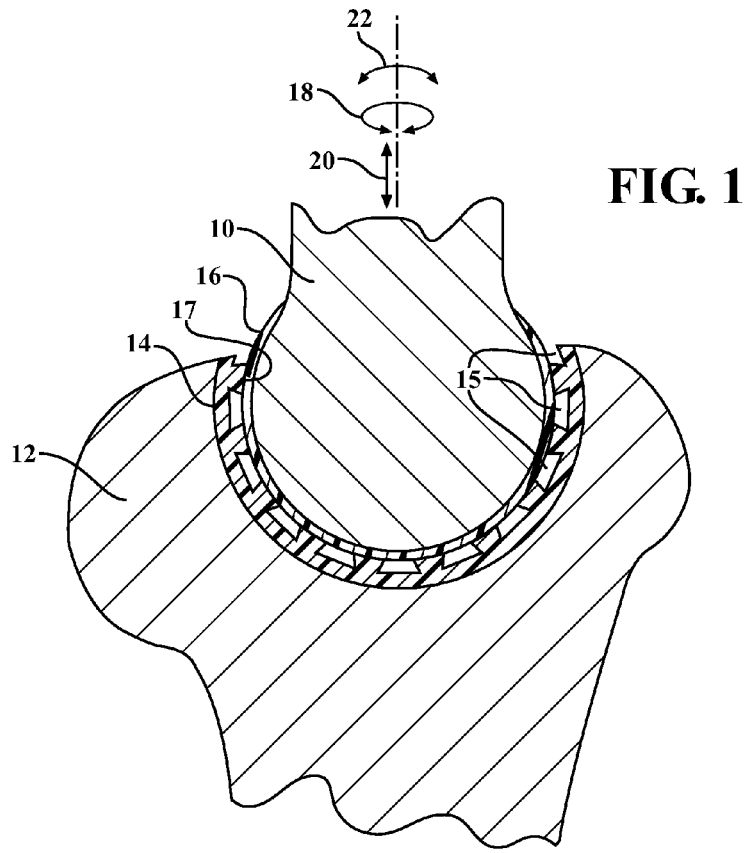
FIG. 1 is an environmental illustration in cutaway of a joint zone depicting a first male portion and a second female receive portion and further illustrating the features of a plastic surface layer applied to the female receiver and exhibiting entrapment pockets for removing worn away debris arising from surface to surface abrading contact with a plasticized layer applied to the male bone.

In view of the above, and referring now to FIG. 1, an illustration in cutaway of a joint zone is depicted including a first male portion 10 and a second female receive portion 12, and further illustrating the features of a plastic surface layer 14 applied to the female (cup shaped) receiver exhibiting a plurality of entrapment pockets, these representatively illustrated by dovetail shaped undercut patterns or reservoirs 15 exhibited by interconnected walls formed into the layer and communicating with discrete surface locations and into which are collected such as finite or microscopic sized shavings or particles which are not shown but are understood to be abraded from continual surface contact established between wear surface 17 associated with first surface layer 14 and opposing wear surface associated with layer 16. As is further defined by any of apertures, channels, grooves or undercut portions as further as shown in each of FIGS. 2A-21, such recessed/undercut patterns operate to remove progressively accumulating and worn away debris, such as arising from surface to surface abrading contact with the male bone 10.

The plasticized layer 16 applied to male bone 10 is illustrated as applied over an exposed joint defining surface. It is envisioned that, additional to the preferred embodiments illustrated and described herein, either or both the male 10 and female 12 portions can exhibit any of a metal (such as titanium) or plastic construction. In particular, it is envisioned that the such a three dimensional joint defining bone constructed of any plastic and/or metal material, with or without a surfacing end material which can likewise include any of the disclosed material compositions, as well as exhibiting a plastic and/or multi-material composite associated with either the substrate or surface portions.

The provision of the surfacing layer 14 (in this instance again associated with the female portion 12) is such that it can include any combination of recesses, valleys, channels and undercut configurations (inverted trapezoidal, T shape or the like). The objective of the layer 14 configuration is to provide generally effective surface support relative the opposing male defined surface (see again at 16) as well as to establish entrapment pockets/canals/undercuts for effectively capturing and removing smaller (including microscopic) sized bits of material abrading from either of the layers 14 or 16 (as well as from a natural or other synthetic surface in the instance of an opposing joint portion which is not otherwise end surface with a plasticized material in the manner shown).

The entrapped bits and pieces of debris material are segregated and contained within the recessed interior and/or undercut defined pockets, such action occurring as a result of natural deflecting/abrading motion occurring between the joint points. Such normal range of motion can include varying combinations of any one or more of rotational motion (arrow 18), linear motion (arrow 20) and/or two-dimensional pivoting motion (arrow 22) established between the ball and receiver joint portions 10 and 12, respectively.

The ability to automatically and effectively remove debris build-up without the requirement of additional medical (e.g. scoping) procedures contributes to extended life of the replacement joint beyond that currently available. Further, and beyond the example shown in FIG. 1, it is also envisioned and understood that the debris entrapment surfacing layer can be incorporated into either (or both) of the male or female joint establishing portions, and it is further envisioned that a first surface applied layer such as identified at 14 can also be employed in combination with a natural bone surface such as associated with ball 10 without the outer applied surface layer 16.

Referring now to FIGS. 2A-21, a series of top plan and size cutaway views are illustrated in a generally planar and non-arcuate fashion of a variety of differently constructed surfacing layers, such as which are understood to be configured as a plasticized mat exhibiting the necessary properties of flexibility for applying across either or both of a male or female joint surface environment. Each succeeding illustration establishes an exemplary and varying recess/undercut pattern incorporated into a joint abrading plasticized surface layer according to any of a number of subset variants of the present invention and which are understood as capable of being applied in any desired bent, folded or pre-arcuate produced manner such that the layer is effectively applied in either of a convex or concave fashion over the male and/or female joint defining surface, such as in the fashion depicted in FIG. 1.

Figure 2A:
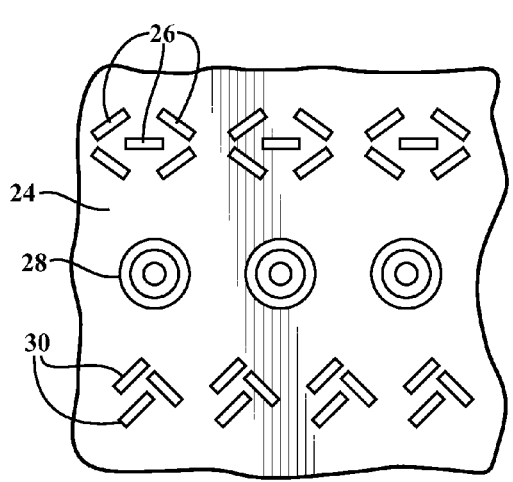
FIGS. 2A-2I illustrate in succession a series of top plan and size cutaway views of a variety of differently configured recess/undercut patterns incorporated into a joint abrading plasticized surface layer according to subset variants of the present invention.

The above said, FIG. 2A illustrates a first alternate example of a mat design 24 exhibiting a first variety of varying recess patterns including those shown at 26, 28 and 30. As illustrated, these can include linear arranged profiles (again at 26 and 30) as well as concentric defined profiles 28. Although not further shown in the two dimensional plan view provided, it is understood that the recess portions can include any of recess channel or enlarged/undercut defined portions formed to a specified depth, which is usually but not necessarily less than a total depth of the plastic layer.

Figure 2B:
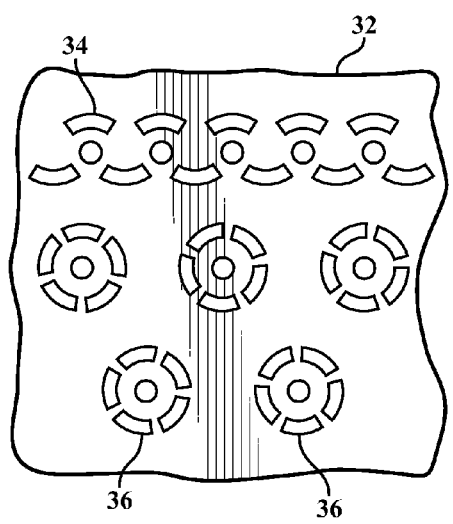
Figure 2C:
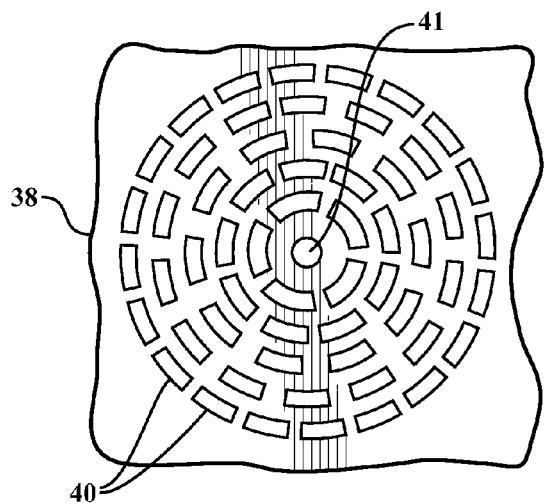
Figure 2D:
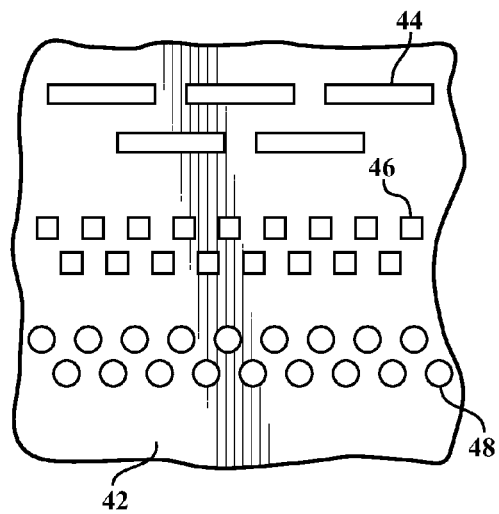

FIG. 2B illustrates a further mat design 32 incorporating a first pattern 34 combining arcuate and circle shaped recess portions, as well as a second pattern 36 exhibiting a modified arrangement in which individual pluralities of segmented arcuate portions surround a central positioned recess. FIG. 2C establishes a further layer 38 with another pattern with succeeding and concentric defined pluralities of segmented portions 40 terminating at a center most located recess or undercut portion 41. FIG. 2D illustrates a similar layer 42 including any of a number of discrete recess/undercut patterns including each of rectangular shapes 44, square shapes 46 and circular shapes 48, each further of a given size and dispersion pattern.

Figure 2E:
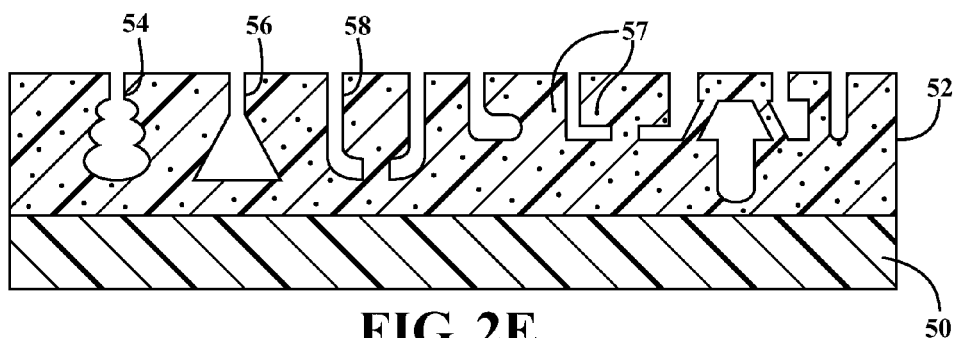
Figure 2F:
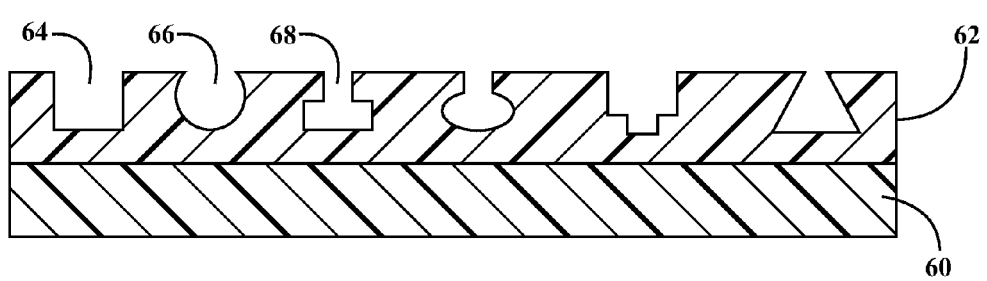

Referring further to FIGS. 2E and 2F, side cutaway illustrations are shown of a pair of composite plastic surfacing layers. As first shown in FIG. 2E, the illustrated layer includes a first harder plastic substratum layer 50, over which is integrally formed an upper/exposed and softer plastic layer 52 and within which is defined any number of alternately configured undercut patterns 54 (snow man), 56 (pseudo-conical/trapezoidal), 58 (modified "J" shape), et. seq. Also collectively depicted at 57 are entrained smaller volumes (such as according to a graded particulate) of either or both a graphite/carbon and/or a ceramic/metallic impregnate material.

A similar arrangement is shown in FIG. 2F and which illustrates a like harder plastic substratum layer 60 over which is molded or otherwise integrally bonded a softer upper layer 62 incorporating a further variety of undercut configured portions 64 (square), 66 (pseudo-spherical), 68 (inverted "T" shape), et seq.

Figure 2G:
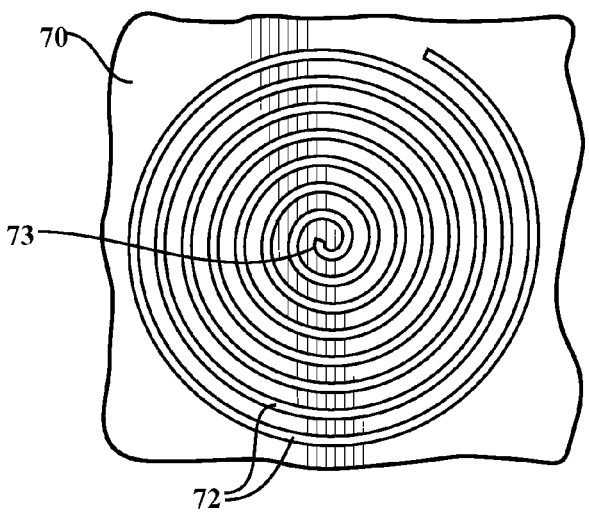
Figure 2H:
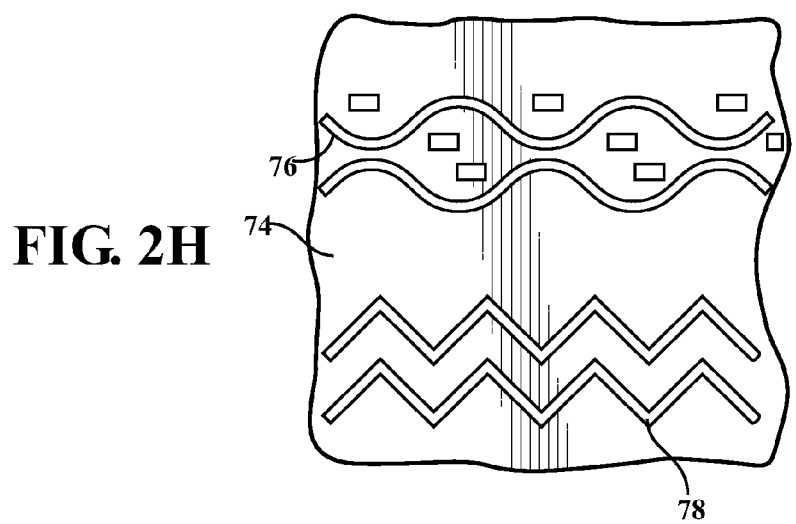
Figure 2I:
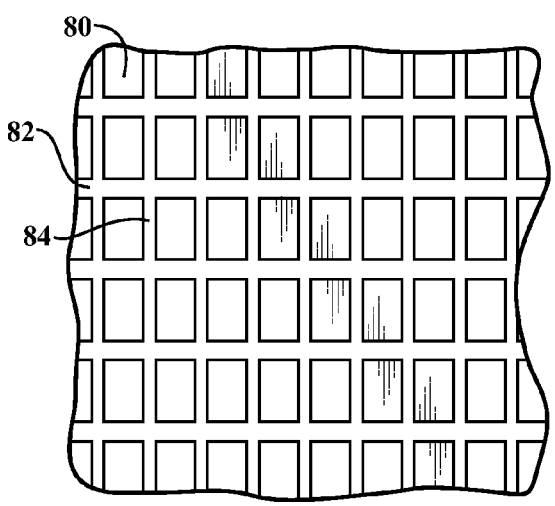

Remaining plan view illustrations FIGS. 2G, 2H and 2I depict other potential configurations and include, as shown in FIG. 2G, a layer 70 of specified thickness incorporating a recess and/or undercut defined spiral configured pattern, see windings 72, and which generally concludes at a central end location 73. FIG. 2H illustrates another layer 74 (again including either an integral or multi-material composition plastic) with additional designated pattern designs 76 and 78.

Finally, FIG. 2I illustrates a yet further plastic layer 80 with a grid shape undercut or recess design including first widthwise extending and spaced apart channels 82 which are intersected by lengthwise (crosswise) extending channels 84. The series of rectangular spaced elements making up the plastic layer 80 and which are intersected by the channels can adopt any alternate configuration based upon the reconfiguration of the intersecting channel grid. It is further envisioned that the channels 82 and 84 can be laid out in a non-linear and/or non-perpendicularly intersecting fashion in order to establish any desired profile, such as further including the composition of grid-like channels in combination with dispersed, enlarged and communicating retention pockets also formed in the associated wear layer.

As depicted in any of the cutaway views of FIGS. 1, 2E and 2F, it is again understood that each of the patterns also shown by non-limiting example in FIGS. 2A, 2B, 2C, 2D, 2G, 2H and 2I can exhibit any undercut or other suitable recess configuration which is intended to assist in segregated removal of accumulated wear debris while maintaining the operational efficiency and integrity of the joint wear zone.

Having described my invention, other additional preferred embodiments will become apparent to those skilled in the art to which it pertains, and without deviating from the scope of the appended claims.

I claim:

1. An implantable artificial layer established between male and female joint defining portions of first and second bones, said layer comprising:
    a mat having a specified shape and size and which is adapted to being secured over a selected one of the joint defining portions, said mat exhibiting either of a concave or a convex first wear surface and establishing an opposing and eccentrically supporting arrangement relative to a second wear surface associated with the other joint defining portion, said second wear surface further exhibiting the other of a concave or convex surface to permit articulation relative to said mat;
    a plurality of volume defining recesses arranged in distributed, spaced apart and undercut extending fashion within said mat, said volume defining recesses each exhibiting a narrow-most passageway in communication with said surface of said mat, a three dimensional undercut profile in communication with said narrow-most passageway further including a snowman such that a maximum interior width dimension of a selected undercut profile is at least a factor of two times greater than a width dimension of said passageway in communication with said wear surface; and
    upon abrading contact between said wear surfaces associated with the joint defining portions, accumulated debris resulting from such contact being segregated from a joint zone established between said wear surfaces and becoming entrapped within said undercut and volume defining recesses.

2. The layer as described in claim 1, said mat including a first harder plastic substratum and a second softer plastic surface.

3. The layer as described in claim 2, additional selected volume defining recesses further comprising undercut defined patterns selected from any of circular, linear and arcuate designs.

4. The layer as described in claim 1, said mat further comprising an antimicrobial plastic.

5. The layer as described in claim 1, said mat including a first additive selected from at least one of a carbon and a graphite and a second additive selected from at least one of a ceramic and a metal for providing the flexible and polymeric based mat with enhanced wear resistant properties.

* * * * *